US008488748B2

(12) United States Patent
Clawson (10) Patent No.: US 8,488,748 B2
(45) Date of Patent: Jul. 16, 2013

(54) MENINGITIS DIAGNOSTIC AND INTERVENTION TOOL FOR EMERGENCY DISPATCH (76) Inventor: Jeffrey J. Clawson, Salt Lake City, UT (US)

( * ) Notice: Subject to any disclaimer, the term of this patent is extended or adjusted under 35 U.S.C. 154(b) by 0 days.

(21) Appl. No.: 13/354,116

(22) Filed: Jan. 19, 2012

(65) Prior Publication Data
US 2012/0183128 A1 Jul. 19, 2012

Related U.S. Application Data (60) Provisional application No. 61/434,340, filed on Jan. 19, 2011.

(51) Int. Cl.
H04M 11/00 (2006.01)
(52) U.S. Cl.
USPC .............................................. 379/45; 379/37
(58) Field of Classification Search
USPC ....................................................... 379/45, 37
See application file for complete search history.

(56) References Cited

U.S. PATENT DOCUMENTS

| 3,799,147 | A | 3/1974 | Adolph et al. |
|---|---|---|---|
| 4,130,881 | A | 12/1978 | Haessler et al. |
| 4,164,320 | A | 8/1979 | Irazoqui et al. |
| 4,237,344 | A | 12/1980 | Moore |
| 4,290,114 | A | 9/1981 | Sinay |
| 4,338,493 | A | 7/1982 | Stenhuis et al. |
| 4,360,345 | A | 11/1982 | Hon |
| 4,455,548 | A | 6/1984 | Burnett |
| 4,489,387 | A | 12/1984 | Lamb et al. |
| 4,731,725 | A | 3/1988 | Suto et al. |
| 4,839,822 | A | 6/1989 | Dormond et al. |
| 4,858,121 | A | 8/1989 | Barber et al. |
| 4,865,549 | A | 9/1989 | Sonsteby |
| 4,922,514 | A | 5/1990 | Bergeron et al. |
| 4,926,495 | A | 5/1990 | Comroe et al. |

(Continued)

FOREIGN PATENT DOCUMENTS

| JP | 2003109162 A | 4/2003 |
|---|---|---|
| JP | 2003-187003 A | 7/2003 |

(Continued)

OTHER PUBLICATIONS

Radosevich, Lynda, "Network holds sway on life, death," Computerworld, v27 n21, May 24, 1993, 2 pgs.

(Continued)

Primary Examiner — Stella Woo
(74) Attorney, Agent, or Firm — John R. Thompson; Stoel Rives LLP (57) ABSTRACT Systems and methods to assist an emergency medical dispatcher in responding to emergency calls are disclosed. A computer-implemented emergency dispatch protocol is provided that includes interrogatories for a dispatcher to ask a caller to generate an appropriate response. A diagnostic tool is provided to aid a dispatcher in determining a likelihood that the patient has meningitis. The diagnostic tool determines a likelihood that the patient has meningitis based on caller-relayed information concerning the caller's observations of the patient. The diagnostic tool can be launched automatically by the emergency dispatch protocol, or manually, as desired by a dispatcher. The diagnostic tool presents a user interface that may provide, among other things, questions to guide the caller in identifying signs and symptoms that the patient has meningitis and input components associated with the questions.

25 Claims, 7 Drawing Sheets

U.S. PATENT DOCUMENTS

| | | | |
|---|---|---|---|
| 4,945,476 A | 7/1990 | Bodick et al. | |
| 4,967,754 A | 11/1990 | Rossi | |
| 5,063,522 A | 11/1991 | Winters | |
| 5,065,315 A | 11/1991 | Garcia | |
| 5,072,383 A | 12/1991 | Brimm et al. | |
| 5,077,666 A | 12/1991 | Brimm et al. | |
| 5,086,391 A | 2/1992 | Chambers | |
| 5,109,399 A | 4/1992 | Thompson | |
| 5,122,959 A | 6/1992 | Nathanson et al. | |
| 5,193,855 A | 3/1993 | Shamos | |
| 5,228,449 A | 7/1993 | Christ et al. | |
| 5,253,164 A | 10/1993 | Holloway et al. | |
| 5,255,187 A | 10/1993 | Sorensen | |
| 5,291,399 A | 3/1994 | Chaco | |
| 5,323,444 A | 6/1994 | Ertz et al. | |
| 5,339,351 A | 8/1994 | Hoskinson et al. | |
| 5,348,008 A | 9/1994 | Bornn et al. | |
| 5,379,337 A | 1/1995 | Castillo et al. | |
| 5,404,292 A | 4/1995 | Hendrickson | |
| 5,410,471 A | 4/1995 | Alyfuku et al. | |
| 5,423,061 A | 6/1995 | Fumarolo et al. | |
| 5,438,996 A | 8/1995 | Kemper et al. | |
| 5,441,047 A | 8/1995 | David et al. | |
| 5,462,051 A | 10/1995 | Oka et al. | |
| 5,471,382 A | 11/1995 | Tallman et al. | |
| 5,502,726 A | 3/1996 | Fischer | |
| 5,513,993 A | 5/1996 | Lindley et al. | |
| 5,516,702 A | 5/1996 | Senyei et al. | |
| 5,521,812 A | 5/1996 | Feder et al. | |
| 5,536,084 A | 7/1996 | Curtis et al. | |
| 5,544,649 A | 8/1996 | David et al. | |
| 5,554,031 A | 9/1996 | Moir et al. | |
| 5,590,269 A | 12/1996 | Kruse et al. | |
| 5,594,638 A | 1/1997 | Iliff | |
| 5,594,786 A | 1/1997 | Chaco et al. | |
| 5,596,994 A | 1/1997 | Bro | |
| 5,630,125 A | 5/1997 | Zellweger | |
| 5,636,873 A | 6/1997 | Sonsteby | |
| 5,650,995 A | 7/1997 | Kent | |
| 5,660,176 A * | 8/1997 | Iliff | 600/300 |
| 5,675,372 A | 10/1997 | Aguayo, Jr. et al. | |
| 5,682,419 A | 10/1997 | Grube et al. | |
| 5,684,860 A | 11/1997 | Milani et al. | |
| 5,689,229 A | 11/1997 | Chaco et al. | |
| 5,719,918 A | 2/1998 | Serbetciouglu et al. | |
| 5,722,418 A | 3/1998 | Bro | |
| 5,724,983 A | 3/1998 | Selker et al. | |
| 5,734,706 A | 3/1998 | Windsor et al. | |
| 5,745,532 A | 4/1998 | Campana, Jr. | |
| 5,748,907 A | 5/1998 | Crane | |
| 5,754,960 A | 5/1998 | Downs et al. | |
| 5,759,044 A | 6/1998 | Redmond | |
| 5,761,278 A | 6/1998 | Pickett et al. | |
| 5,761,493 A | 6/1998 | Blakeley et al. | |
| 5,787,429 A | 7/1998 | Nikolin, Jr. | |
| 5,805,670 A | 9/1998 | Pons et al. | |
| 5,809,493 A | 9/1998 | Ahamed et al. | |
| 5,822,544 A | 10/1998 | Chaco et al. | |
| 5,823,948 A | 10/1998 | Ross, Jr. et al. | |
| 5,826,077 A | 10/1998 | Blakeley et al. | |
| 5,832,187 A | 11/1998 | Pedersen et al. | |
| 5,842,173 A | 11/1998 | Strum et al. | |
| 5,844,817 A | 12/1998 | Lobley et al. | |
| 5,850,611 A | 12/1998 | Krebs | |
| 5,857,966 A | 1/1999 | Clawson | |
| 5,901,214 A | 5/1999 | Shaffer et al. | |
| 5,902,234 A | 5/1999 | Webb | |
| 5,910,987 A | 6/1999 | Ginter et al. | |
| 5,912,818 A | 6/1999 | McGrady et al. | |
| 5,915,019 A | 6/1999 | Ginter et al. | |
| 5,926,526 A | 7/1999 | Rapaport et al. | |
| 5,933,780 A | 8/1999 | Connor et al. | |
| 5,961,446 A | 10/1999 | Beller et al. | |
| 5,962,891 A | 10/1999 | Arai | |
| 5,964,700 A | 10/1999 | Tallman et al. | |
| 5,986,543 A | 11/1999 | Johnson | |
| 5,989,187 A | 11/1999 | Clawson | |
| 5,991,730 A | 11/1999 | Lubin et al. | |
| 5,991,751 A | 11/1999 | Rivette et al. | |
| 6,004,266 A | 12/1999 | Clawson | |
| 6,010,451 A | 1/2000 | Clawson | |
| 6,022,315 A | 2/2000 | Iliff | |
| 6,035,187 A | 3/2000 | Franza | |
| 6,040,770 A | 3/2000 | Britton | |
| 6,052,574 A | 4/2000 | Smith, Jr. | |
| 6,053,864 A | 4/2000 | Clawson | |
| 6,058,179 A | 5/2000 | Shaffer et al. | |
| 6,074,345 A | 6/2000 | van Oostrom et al. | |
| 6,076,065 A | 6/2000 | Clawson | |
| 6,078,894 A | 6/2000 | Clawson et al. | |
| 6,106,459 A | 8/2000 | Clawson | |
| 6,112,083 A | 8/2000 | Sweet et al. | |
| 6,115,646 A | 9/2000 | Fiszman et al. | |
| 6,117,073 A | 9/2000 | Jones et al. | |
| 6,118,866 A | 9/2000 | Shtivelman | |
| 6,127,975 A | 10/2000 | Maloney | |
| 6,134,105 A | 10/2000 | Lueker | |
| 6,292,542 B1 | 9/2001 | Bilder | |
| 6,370,234 B1 | 4/2002 | Kroll | |
| 6,535,121 B2 | 3/2003 | Matheny | |
| 6,594,634 B1 | 7/2003 | Hampton et al. | |
| 6,607,481 B1 | 8/2003 | Clawson | |
| 6,610,012 B2 | 8/2003 | Mault | |
| 6,696,956 B1 | 2/2004 | Uchida et al. | |
| 6,879,819 B2 | 4/2005 | Brooks | |
| 6,901,397 B1 | 5/2005 | Moldenhauer et al. | |
| 6,931,112 B1 | 8/2005 | McFarland et al. | |
| 6,968,375 B1 | 11/2005 | Brown | |
| 7,106,835 B2 | 9/2006 | Saalsaa | |
| 7,194,395 B2 | 3/2007 | Genovese | |
| 7,289,944 B1 | 10/2007 | Genovese | |
| 7,428,301 B1 | 9/2008 | Clawson | |
| 7,436,937 B2 | 10/2008 | Clawson | |
| 7,645,234 B2 | 1/2010 | Clawson | |
| 7,703,020 B2 | 4/2010 | Bhattaru | |
| 7,783,586 B2 | 8/2010 | Friedlander et al. | |
| 7,978,826 B2 | 7/2011 | Salafia et al. | |
| 8,294,570 B2 | 10/2012 | Clawson | |
| 8,335,298 B2 * | 12/2012 | Clawson | 379/45 |
| 2002/0004729 A1 | 1/2002 | Zak et al. | |
| 2002/0106059 A1 | 8/2002 | Kroll et al. | |
| 2003/0028536 A1 | 2/2003 | Singh et al. | |
| 2003/0050538 A1 | 3/2003 | Naghavi et al. | |
| 2003/0187615 A1 | 10/2003 | Epler et al. | |
| 2003/0195394 A1 | 10/2003 | Saalsaa | |
| 2003/0212575 A1 | 11/2003 | Saalsaa et al. | |
| 2006/0059423 A1 | 3/2006 | Lehmann et al. | |
| 2006/0122520 A1 | 6/2006 | Banet et al. | |
| 2006/0167346 A1 | 7/2006 | Sarel | |
| 2006/0173500 A1 | 8/2006 | Walker et al. | |
| 2006/0178908 A1 | 8/2006 | Rappaport | |
| 2006/0212315 A1 | 9/2006 | Wiggins | |
| 2007/0055559 A1 | 3/2007 | Clawson | |
| 2007/0112275 A1 | 5/2007 | Cooke et al. | |
| 2007/0116189 A1 | 5/2007 | Clawson | |
| 2007/0201664 A1 * | 8/2007 | Salafia et al. | 379/201.01 |
| 2008/0310600 A1 | 12/2008 | Clawson | |
| 2009/0168975 A1 | 7/2009 | Clawson | |
| 2009/0191529 A1 | 7/2009 | Mozingo et al. | |
| 2010/0004710 A1 | 1/2010 | Kellum | |
| 2010/0121156 A1 | 5/2010 | Yoo | |
| 2010/0152800 A1 | 6/2010 | Walker et al. | |
| 2010/0198755 A1 | 8/2010 | Soll et al. | |
| 2010/0257250 A1 | 10/2010 | Salafia et al. | |
| 2011/0064204 A1 | 3/2011 | Clawson | |
| 2011/0066002 A1 | 3/2011 | Clawson | |
| 2011/0099031 A1 | 4/2011 | Nair | |
| 2011/0205052 A1 | 8/2011 | Clawson | |
| 2011/0215930 A1 | 9/2011 | Lee et al. | |
| 2012/0207286 A1 | 8/2012 | Clawson | |
| 2012/0210271 A1 | 8/2012 | Clawson | |

FOREIGN PATENT DOCUMENTS

| | | |
|---|---|---|
| JP | 2003-256963 A | 12/2003 |
| JP | 2010-033201 A | 12/2010 |
| KR | 10-2005-0085778 A | 8/2005 |
| KR | 10-2006-0084866 A | 7/2006 |

| | | |
|---|---|---|
| KR | 20070043337 A | 4/2007 |
| KR | 10-2008-0004125 A | 1/2008 |
| WO | WO 2004030259 | 4/2004 |
| WO | WO 2006/015229 A2 | 2/2006 |
| WO | WO 2008/156876 A1 | 12/2008 |

OTHER PUBLICATIONS

Harris, Roger, "Updated 911 Phone System Top Concern of Residents," Business First-Louisville, v9 n19 s1, Dec. 1992, 3 pgs.
"Geac Completes Software Install," Wireless Week, Nov. 18, 1996, 3 pgs.
"Dictaphone introduces Windows-based Computer-Aided Dispatch (CAD) system," Business Wire, Apr. 23, 1996, 2 pgs. (in commercial use in 1995).
Holroyd, Brian, et al., "Medical Control; Quality Assurance in Prehospital Care," JAMA, the Journal of American Medical Association, v256, n8, Aug. 1986, p. 1027-1031.
CBS web page News Story entitled "911 Operator: 'It's got to be Hell'", Mar. 31, 2006 (excerpts from 911 operators' actions during the attacks on Sep. 11, 2001), 3 pgs.
Best, Wendy, "999 United Emergency services share life-saving Role to boost response," Western Daily Press, WDP Severnside ed., May 27, 1999, 2 pgs.
Poellmitz, William C., "Wireless technology keeps public safety a step ahead," Nation's Cities Weekly, v21 n17, Apr. 27, 1998, 3 pgs.
Crowley, Mark, "Learning from CAD System Implementation," Communications, v29 n8, Aug. 1992, 5 pgs.
Anonymous, "Suburban Chicago towns centralize 911 services," Communications News, v31 n10, Oct. 1994, 2 pgs.
Office Action Summary from USPTO for U.S. Appl. No. 10/255,901 mailed Dec. 31, 2003, 8 pgs.
Office Action Summary from USPTO for U.S. Appl. No. 10/255,901 mailed Oct. 13, 2004, 8 pgs.
Office Action Summary from USPTO for U.S. Appl. No. 10/255,901 mailed Jun. 29, 2005, 7 pgs.
Advisory Action Before the Filing of an Appeal Brief from USPTO for U.S. Appl. No. 10/255,901 mailed Feb. 14, 2006, 3 pgs.
Office Action Summary from USPTO for U.S. Appl. No. 10/255,901 mailed Jun. 7, 2006, 8 pgs.
Office Action Summary from USPTO for U.S. Appl. No. 10/255,901 mailed Feb. 27, 2007, 8 pgs.
Office Action Summary from USPTO for U.S. Appl. No. 10/255,901 mailed Sep. 6, 2007, 9 pgs.
Office Action Summary from USPTO for U.S. Appl. No. 10/255,905 mailed May 19, 2004, 7 pgs.
Office Action Summary from USPTO for U.S. Appl. No. 10/255,905 mailed May 26, 2005, 5 pgs.
Office Action Summary from USPTO for U.S. Appl. No. 10/255,905 mailed Feb. 9, 2006, 8 pgs.
Advisory Action Before the Filing of an Appeal Brief from USPTO for U.S. Appl. No. 10/255,905 mailed Aug. 11, 2006, 3 pgs.
Office Action Summary from USPTO for U.S. Appl. No. 10/255,905 mailed Jan. 30, 2007, 7 pgs.
Notice of Non-Compliant Amendment (37 CFR 1.121) from USPTO for U.S. Appl. No. 10/255,905 mailed Jul. 9, 2007, 4 pgs.
Office Action Summary from USPTO for U.S. Appl. No. 10/255,905 mailed Oct. 5, 2007, 7 pgs.
Office Action Summary from USPTO for U.S. Appl. No. 09/685,697 mailed Jul. 18, 2003, 8 pgs.
Office Action Summary from USPTO for U.S. Appl. No. 09/685,697 mailed Feb. 3, 2004, 5 pgs.
Office Action Summary from USPTO for U.S. Appl. No. 09/685,697 mailed Jan. 4, 2005, 5 pgs.
Office Action Summary from USPTO for U.S. Appl. No. 09/685,697 mailed Oct. 4, 2005, 7 pgs.
Advisory Action Before the Filing of an Appeal Brief from USPTO for U.S. Appl. No. 09/685,697 mailed Mar. 13, 2006, 4 pgs.
Office Action Summary from USPTO for U.S. Appl. No. 09/685,697 mailed Jun. 26, 2006, 8 pgs.
Office Action Summary from USPTO for U.S. Appl. No. 09/685,697 mailed Apr. 10, 2007, 9 pgs.
Office Action Summary from USPTO for U.S. Appl. No. 09/685,697 mailed Oct. 9, 2007, 11 pgs.
Office Action Summary from USPTO for U.S. Appl. No. 10/140,635 mailed Oct. 3, 2003, 9 pgs.
Office Action Summary from USPTO for U.S. Appl. No. 10/140,635 mailed Jul. 16, 2004, 11 pgs.
Office Action Summary from USPTO for U.S. Appl. No. 10/140,635 mailed Apr. 19, 2005, 11 pgs.
Office Action Summary from USPTO for U.S. Appl. No. 10/140,635 mailed Jan. 17, 2006, 13 pgs.
Office Action Summary from USPTO for U.S. Appl. No. 10/140,635 mailed Sep. 20, 2006, 15 pgs.
Office Action Summary from USPTO for U.S. Appl. No. 10/140,635 mailed Jun. 21, 2007, 15 pgs.
International Search Report for PCT/US2008/054987 filed on Feb. 26, 2008, and mailed on Oct. 8, 2008, 2 pgs.
Written Opinion of the International Searching Authority for PCT/US2008/054987 filed on Feb. 26, 2008, and mailed on Oct. 8, 2008, 9 pgs.
Notification of Transmittal of the ISR (2 pgs.), ISR, (2 pgs.), and Written Opinion (8 pgs.) for PCT/US2009/040909 filed on Apr. 17, 2009; mailed from ISA on Jun. 10, 2009.
International Search Report for PCT/US2009/048577 filed on Jun. 25, 2009, and mailed from ISA on Aug. 7, 2009, 9 pgs.
International Search Report and Written Opinion for PCT/US2010/043311 filed on Jul. 27, 2010, and mailed from ISA on Jan. 19, 2011.
International Search Report and Written Opinion for PCT/US2010/043308 filed on Jul. 27, 2010, and mailed from ISA on Jan. 19, 2011.
Office Action Summary from USPTO for U.S. Appl. No. 12/396,201 mailed Mar. 8, 2011, 23 pgs.
Office Action Summary from USPTO for U.S. Appl. No. 12/268,963 mailed Jul. 29, 2011, 18 pgs.
International Preliminary Report of Patentability for PCT/US2009/048577 filed on Jun. 25, 2009 mailed Oct. 27, 2011, 7 pgs.
International Search Report and Written Opinion for PCT/US2011/042543 filed on Jun. 30, 2011, and mailed from ISA on Feb. 9, 2012, 9 pgs.
International Search Report and Written Opinion for PCT/US2011/042582 filed on Jun. 30, 2011, and mailed from ISA on Feb. 9, 2012, 6 pgs.
International Search Report and Written Opinion PCT/US2010/050402, filed on Sep. 27, 2010, and mailed from ISA on Apr. 27, 2011, 9 pgs.
International Preliminary Report of Patentability for PCT/US2010/043308 filed on Jul. 27, 2010 mailed Mar. 22, 2012, 6 pgs.
International Preliminary Report of Patentability for PCT/US2010/043311 filed on Jul. 27, 2010 mailed Mar. 29, 2012, 6 pgs.
Office Action Summary from USPTO for U.S. Appl. No. 12/558,045 mailed Mar. 22, 2012, 9 pgs.
Office Action Summary from USPTO for U.S. Appl. No. 12/558,808 mailed Apr. 23, 2012, 12 pgs.
Office Action Summary from USPTO for U.S. Appl. No. 12/422,561 mailed Jul. 3, 2012, 23 pgs.
International Search Report and Written Opinion for PCT/US2012/021867 filed Jan. 19, 2012, and mailed Aug. 30, 2012, 9 pgs.
Office Action Summary from USPTO for U.S. Appl. No. 12/422,561 mailed Feb. 1, 2013, 26 pgs.
Notice of Allowance from USPTO for U.S. Appl. No. 13/026,055 mailed Jan. 24, 2013.
Notice of Allowance from USPTO for U.S. Appl. No. 10/255,901 mailed Feb. 20, 2013.
Nordberg, Marie, "Dispatch Disasters," Emergency Medicine, Aug. 1995.

* cited by examiner

MENINGITIS DIAGNOSTIC AND INTERVENTION TOOL FOR EMERGENCY DISPATCH

RELATED APPLICATIONS

This application claims the benefit under 35 U.S.C. §119(e) of U.S. Provisional Patent Application No. 61/434,340, filed Jan. 19, 2011, and titled "MENINGITIS DIAGNOSTIC AND INTERVENTION TOOL FOR EMERGENCY DISPATCH," which is hereby incorporated by reference herein in its entirety.

COPYRIGHT NOTICE

©2011 Priority Dispatch Corp. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR §1.71(d).

TECHNICAL FIELD

This disclosure relates to computer systems and methods for providing medical protocol interrogation, instruction, and emergency dispatch. More specifically, the disclosure is directed to computer-implemented tools to assist a dispatcher during an interrogation and instruction of an emergency caller.

BRIEF DESCRIPTION OF THE DRAWINGS

Non-limiting and non-exhaustive embodiments of the disclosure are described, including various embodiments of the disclosure with reference to the figures, in which.

DETAILED DESCRIPTION

Emergency dispatchers handle emergency calls reporting a wide variety of emergency situations. An automated emergency dispatch system, which may be implemented on a computer, can aid a dispatcher in prioritizing the calls and processing the calls to generate an appropriate emergency dispatch response. Regardless of the experience or skill level of the dispatcher, automated emergency dispatch systems can enable a consistent and predictable emergency dispatch response, despite the diverse aspects of emergency situations, including inter alia signs, symptoms, conditions, and circumstances, that may be reported from one call to the next.

Although an automated emergency dispatch system can enable collection and processing of widely divergent aspects of emergency situations, some of the emergency situations and/or aspects reported should be explored in greater depth as they are reported. This further exploration may require the dispatcher to probe more deeply to gather more descriptive details. Moreover, some emergency situations may be improved by more detailed instructions. Still other emergency situations may involve a clinical presentation of a condition that is not easily diagnosed, but which could alter the appropriate dispatch response if properly diagnosed.

A dispatcher with little or no medical training or experience likely cannot properly explore situations and/or aspects or diagnose medical conditions, let alone instruct a caller to do so. Furthermore, the automated emergency dispatch systems are not equipped to assist or enable a dispatcher to explore situations in greater depth, to provide further instruction, or to diagnose conditions. Accordingly, the present disclosure is directed to diagnostic tools that supplement an automated emergency dispatch system to attempt to address these and other shortcomings of automated emergency dispatch systems.

The embodiments of the disclosure will be best understood by reference to the drawings, wherein like parts are designated by like numerals throughout. It will be readily understood that the components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified.

In some cases, well-known features, structures or operations are not shown or described in detail. Furthermore, the described features, structures, or operations may be combined in any suitable manner in one or more embodiments. It will also be readily understood that the components of the embodiments as generally described and illustrated in the figures herein could be arranged and designed in a wide variety of different configurations.

Several aspects of the embodiments described will be illustrated as software modules or components. As used herein, a software module or component may include any type of computer instruction or computer executable code located within a memory device and/or computer-readable storage medium. A software module may, for instance, comprise one or more physical or logical blocks of computer instructions, which may be organized as a routine, program, object, component, data structure, etc. that performs one or more tasks or implements particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Suitable software to assist in implementing the invention is readily provided by those of skill in the pertinent art(s) using the teachings presented here and programming languages and tools, such as Java, Pascal, C++, C, database languages, APIs, SDKs, assembly, firmware, microcode, and/or other languages and tools.

An emergency dispatch system as disclosed herein may be computer-implemented in whole or in part on a digital computer. The digital computer includes a processor performing the required computations. The computer further includes a memory in electronic communication with the processor for storing a computer operating system. The computer operating systems may include MS-DOS, Windows, Linux, Unix, AIX, CLIX, QNX, OS/2, and Apple. Alternatively, it is expected that future embodiments will be adapted to execute on other future operating systems. The memory also stores application programs including a Computer Aided Dispatch (CAD) program, an automated emergency dispatch protocol, a user interface program, and data storage. The computer may further include an output device, such as a display unit, for viewing the displayed instructions and inquiries, and a user input device for inputting response data.

Figure 1:
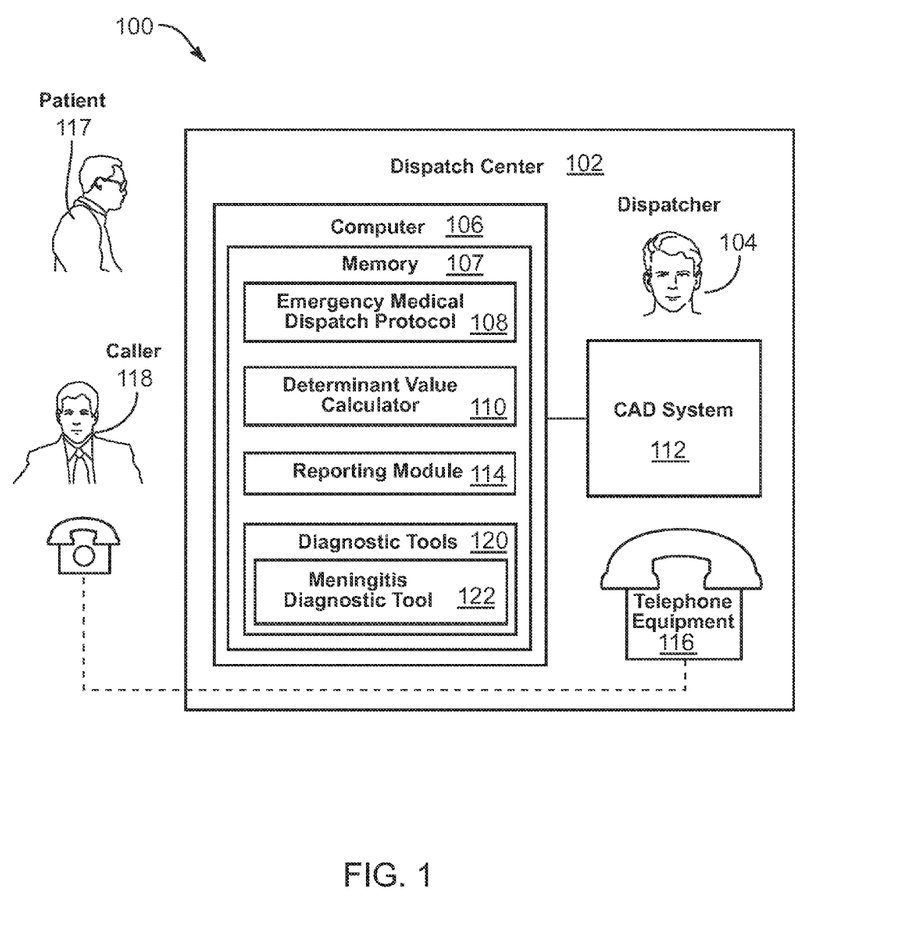
FIG. 1 is a block diagram of an emergency medical dispatch system, according to one embodiment.

FIG. 1 is an emergency medical dispatch system 100, according to one embodiment. At a dispatch center 102, a dispatcher 104 may operate a computer 106. The computer 106 may include a memory 107 to store protocols, modules, tools, data, etc. The computer 106 may be configured to execute an emergency medical dispatch protocol 108 to enable the dispatcher 104 to rapidly and consistently address a medical emergency of a patient 117 as reported by a caller 118. The emergency medical dispatch protocol 108 provides a logic tree with questions, possible responses from a caller 118, and instructions to the caller 118. The responses may route to subsequent questions and/or instructions to the caller. The responses are processed according to predetermined logic to provide to the dispatcher 104 the correct emergency medical dispatch response (e.g., by trained emergency responders) and the appropriate doctor-approved post-dispatch instructions for relay to the caller 118 before professional help arrives at the scene. The emergency medical dispatch system 100 may also aid the dispatcher in determining an appropriate priority of the emergency call, including but not limited to a priority of the emergency call relative to other emergency calls.

Although an emergency medical dispatch system 100 and emergency medical dispatch protocol 108 are disclosed and described herein, a person of ordinary skill can appreciate that other emergency dispatch systems and emergency dispatch protocols are contemplated, including but not limited to emergency fire dispatch systems and protocols and emergency police dispatch systems and protocols. Exemplary embodiments of such emergency dispatch systems and protocols are disclosed in U.S. Pat. Nos. 5,857,966, 5,989,187, 6,004,266, 6,010,451, 6,053,864, 6,076,065, 6,078,894, 6,106,459, 6,607,481, 7,106,835, and 7,428,301, which are incorporated herein by reference.

The computer 106 may also operate a determinant value calculator 110 to calculate a determinant value from the responses of the caller 118 to protocol questions. The computer 106 presents the determinant value to generate an appropriate emergency dispatch response and/or establish the priority of the emergency call. The response may include dispatching professional emergency responders to the scene of the emergency. Because the questions asked and the recommendations that are made deal directly with life and death decisions, the protocols used shall have passed through a rigorous medical review by a panel of doctors and EMS public safety experts who specialize in emergency medicine. The determinant value calculator 110 may be stored on the memory 107 of the computer.

Many calls for medical services are not true medical emergencies, so it is important to prioritize the calls in several ways. First, calls that are true emergencies should be dispatched first. Second, if an agency has units with different capabilities, the more advanced units should be sent to more severe medical problems. And finally, if lights-and-siren are not needed from a medical standpoint, they should not be used, thereby increasing the safety of all those on the road and in the emergency vehicles. While many medical calls are not true emergencies, all situations can benefit from medical evaluation and instruction. Prior to the arrival of professional help on-scene, the emergency medical dispatch protocol 108 can provide the dispatcher 104 with instructions for the caller 118 that are appropriate to the type of call, from a patient 117 with minor lacerations to a patient 117 who is not breathing.

The determinant value provides a categorization code of the type and level of the incident. The code may be provided to a Computer Aided Dispatch (CAD) system 112 for processing. The CAD system 112 is a tool used by a dispatcher 104 to track and allocate emergency response resources. The CAD system 112 may operate in whole or in part on a separate computer in communication with the computer 106. In another embodiment, the CAD system 112 operates on the computer 106. The primary information used by the CAD system 112 is location information of both the incident and units, unit availability and the type of incident. The CAD system 112 may use third party solutions, vehicle location transponders and mobile data terminals (MDT's) for automating the location and availability tasks. The CAD system may also use an emergency medical dispatch protocol 108 to facilitate structured call taking for incident interrogation, as previously described.

The computer 106 may also include a reporting module 114 to statistically measure the performance of individual staff and overall performance of the dispatch center 102. These statistics include compliance rates, call processing statistics, and peer measurements. The reporting module 114 may be stored on the memory 107 of the computer 106.

The computer 106 may further comprise an input device, such as a keyboard, mouse, or other input device, and also an output device such as a display monitor. The input device receives input from a user (generally a dispatcher) and provides it to the emergency medical dispatch system 100. The input may be provided to the computer 106, the emergency medical dispatch protocol 108, the diagnostic tools 120, and/or the CAD system 112. An output device receives output from the emergency medical dispatch system 100 and displays or otherwise presents the output to the user. In another embodiment, the input device and the output device are provided by the CAD system 112. In still another embodiment, the CAD system 112 runs on the computer 106.

The dispatch center 102 includes telephony equipment 116 to answer emergency calls. A call into the dispatch center 102 from a caller 118 may initiate creation of a medical call incident. The dispatcher 104 identifies the call as requiring an emergency medical dispatch, and the emergency medical dispatch protocol 108 is accessed. The emergency medical dispatch protocol 108 may provide instructions that are expertly drafted to assist a novice caller 118 in diagnosing a condition of a patient 117. The emergency medical dispatch protocol 108 may also provide expertly drafted first aid instructions to assist a patient 117 prior to the arrival of trained emergency responders. The instructions may be vocally relayed by the dispatcher 104 to the caller 118 over the telephony equipment 116.

Some of the questions presented by the emergency medical dispatch protocol 108 may be readily answerable by the caller 118, whereas others are more difficult to answer. Certain diagnostic inquiries may be difficult for the untrained caller to determine or may be difficult to answer under the stress of an emergency situation. For example, the caller may have a difficult time diagnosing whether a patient has meningitis. Accordingly, in addition to instructions, the emergency medical dispatch system 100 may provide one or more computer-implemented diagnostic tools 120. The diagnostic tools 120 may greatly improve information collection and intervention for emergency medical response situations and aid in saving lives.

A diagnostic tool 120 may aid the dispatcher 104 and/or the caller 118 (via instructions from the dispatcher 104) in diagnosing a condition of a patient 117. A diagnostic tool 120 may also be an interventional tool, providing instructions that direct a caller 118 to intervene, or take action, to treat a patient 117, or otherwise change the circumstances or conditions of an emergency situation. For sake of clarity, diagnostic tools and interventional tools are both referred to herein generally as diagnostic tools. Accordingly, a diagnostic tool 120, as referred to herein, may provide diagnostic instructions, interventional instructions, or both diagnostic and interventional instructions. Whether a diagnostic tool 120 provides merely diagnostic instructions, merely interventional instructions, or both diagnostic and interventional instructions, the diagnostic tool can provide consistent and reliable instruction, information gathering, and/or timing for a particular emergency situation.

The diagnostic tools 120 are computer implemented software modules that enable a dispatcher 104 to provide consistent, expert advice to assist a caller with regards to a particular aspect of an emergency situation. In highly stressful conditions, the diagnostic tools 120 provide a necessary resource to reading critical signs. The diagnostic tools 120 may be stored in the memory 107 of the computer 106 and initiated and executed as required. The diagnostic tools 120 may be embodied as computer executable software applications and associated data.

The emergency medical dispatch protocol 108 may call on a diagnostic tool 120, for example, to assist with an interrogatory, and may route to the appropriate diagnostic tool 120 when needed. When directed according to the protocol 108, the emergency medical dispatch system 100 may automatically, i.e., without dispatcher intervention, initiate the appropriate diagnostic tool 120 on the dispatch center computer 106. This may occur when the emergency medical dispatch protocol 108 arrives at a diagnosis step in the protocol and initiates a corresponding diagnostic tool 120. The emergency medical dispatch system 100 may also allow the dispatcher 104 the option to manually call upon a diagnostic tool 120 as desired. Icons and/or buttons may be displayed in a tool bar, or other convenient location on a user interface to allow the dispatcher 104 to initiate a corresponding diagnostic tool 120. In another embodiment, the emergency medical dispatch protocol 108 may simply prompt the dispatcher 104 to launch the appropriate diagnostic tool 120 when needed.

The diagnostic tool 120 discussed herein comprises a meningitis diagnostic tool 122. The meningitis diagnostic tool 122 may be configured to facilitate diagnosing whether a patient has meningitis, or otherwise assess the likelihood that the patient has meningitis. The meningitis diagnostic tool 122 may effectively assess the likelihood of meningitis regardless of whether the meningitis is bacterial meningitis or viral meningitis. Specifically, the meningitis diagnostic tool 122 may present a user interface providing questions for relay to the caller 118 to guide the caller 118 in identifying the indicators, including signs, symptoms, conditions, circumstances, or other criteria, that indicate the patient 117 may have meningitis. As used herein, the term indicator includes, but is not limited to, signs, symptoms, conditions, circumstances, or other criteria that can be used to diagnose or otherwise assess the patient's medical condition, and particularly the patient's condition as it may relate to meningitis. The questions may probe for the caller's observations of various indicators relating to meningitis. The questions may have a form similar to the interrogatories presented by an emergency dispatch protocol. The user interface may further present input fields to collect dispatcher-entered input indicative of caller-relayed information relating to the caller's observations of the various indicators. The meningitis diagnostic tool 122 may receive the input corresponding to, or otherwise indicative of, the various identified indicators and use the input to make a determination whether the patient has meningitis. The meningitis diagnostic tool 122 is discussed below with reference to figures of graphical user interfaces that exemplify certain embodiments. One of skill in the art will appreciate that such interfaces may be implemented and designed in various ways.

Figure 2:
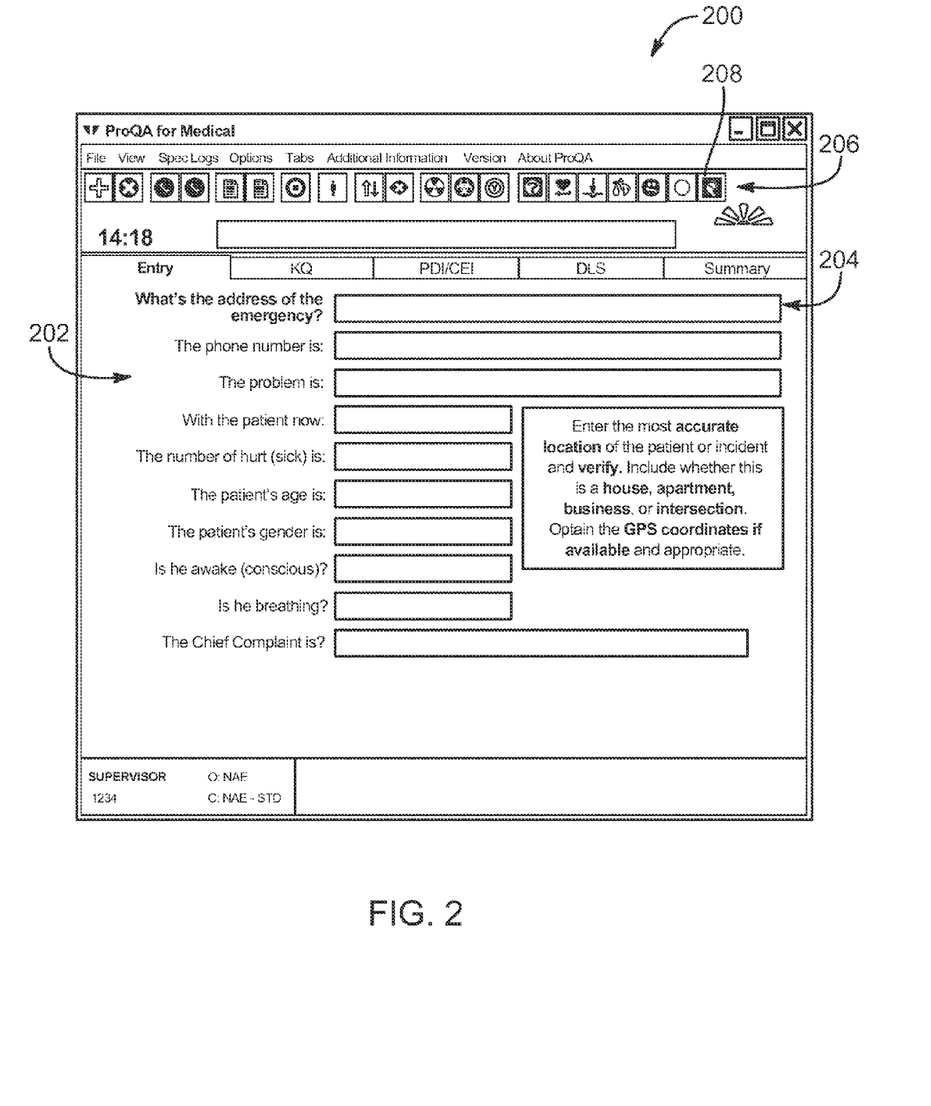
FIG. 2 is a user interface of an emergency medical dispatch system, according to one embodiment.

FIG. 2 illustrates a user interface 200 of an emergency medical dispatch protocol, according to one embodiment. The emergency medical dispatch protocol user interface 200 allows a dispatcher to interface with the emergency medical dispatch protocol. The emergency medical dispatch protocol may present interrogatories 202 via the emergency medical dispatch protocol user interface 200. The interrogatories 202 are provided for the dispatcher to direct to the caller to gather information regarding the medical emergency of the patient. The dispatcher and/or the emergency medical dispatch system may gather the information in the form of caller responses to the interrogatories 202. The dispatcher may input the caller's responses to the interrogatories 202 into response fields 204 provided by the user interface 200. The response fields 204 may include, for example, familiar user interface components, including but not limited to text fields, text boxes, menus, drop-down menus, drop-down selection boxes, lists, buttons, check boxes, and radio buttons. The response fields 204 may correspond to information indicative of one or more responses of the caller to the interrogatories 202.

The caller responses, and information included therein, relayed from the caller to the dispatcher, and entered (or input) into the system, may be used by the emergency medical dispatch protocol to determine subsequent interrogatories 202 and instructions to present to the dispatcher. The caller responses, and information therein, may indicate the caller's observations of indicators of the patient's medical condition, or other information concerning indicators for assessing the patient's medical condition. The information gathered from the caller responses may be used by the emergency medical dispatch system to generate an emergency medical dispatch response by trained emergency responders. The information gathered from the caller responses may be used by the determinant value calculator to calculate a determinant value that can be communicated to the emergency responders. Further details of emergency medical dispatch protocols and user interfaces to interact with the same can be found in the earlier referenced U.S. patents.

The emergency medical dispatch system user interface 200 may also provide one or more diagnostic tool launch input components 206. As illustrated, one or more buttons may be provided on the user interface as diagnostic tool launch input components 206. As will be appreciated by a person of ordinary skill, the diagnostic tool launch input components 206 may comprise a component other than a button, including familiar user interface components such as a drop down menu, a drop down selection box, a list, a check box, and a radio button. The diagnostic tool launch input components 206 enable the dispatcher to launch a particular diagnostic tool. Although the emergency medical dispatch protocol may automatically initiate a diagnostic tool based on dispatcher-entered input indicative of one or more responses of the caller, the diagnostic tool launch input components 206 provide a way for the dispatcher to manually (e.g., anytime, at the dispatcher's discretion) initiate a diagnostic tool. In FIG. 2, the user interface provides a meningitis diagnostic tool launch input component 208. The meningitis diagnostic tool launch input component 208 may comprise a button on the emergency medical dispatch system user interface 200. The button may include an icon, such as an image of an individual's head that is swelling, to indicate that the button is the meningitis diagnostic tool launch input component 208 that manually initiates the meningitis diagnostic tool. In another embodiment, the button may include a label to convey that the button is the meningitis diagnostic tool launch input component 208.

Figure 3A:
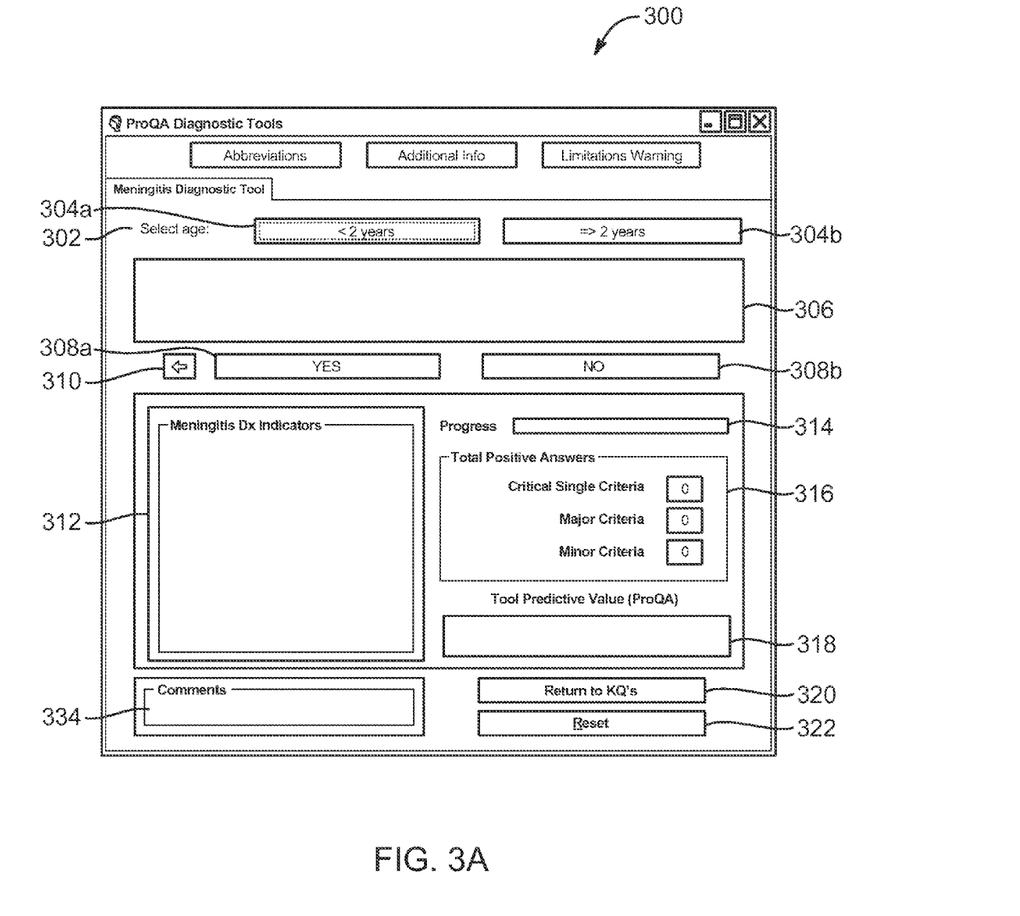
FIGS. 3A-3C are embodiments of a user interface of a meningitis diagnostic tool.
Figure 3B:
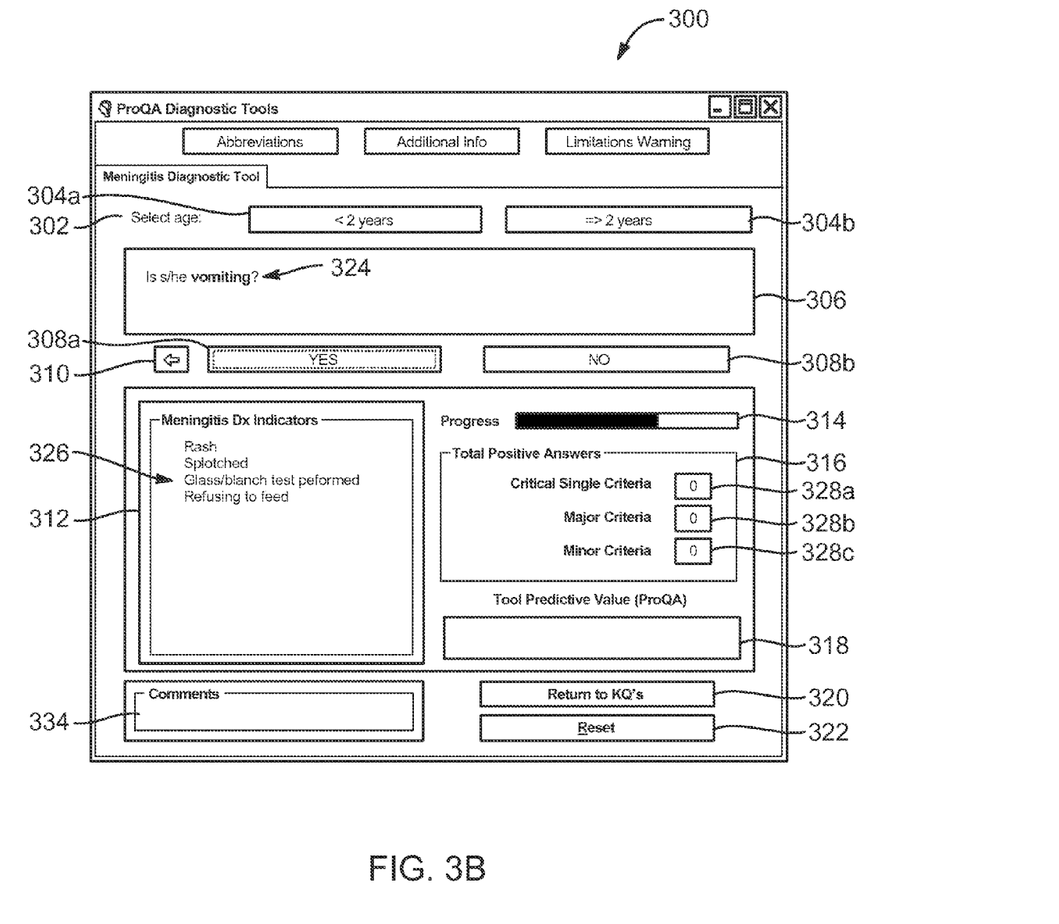
Figure 3C:
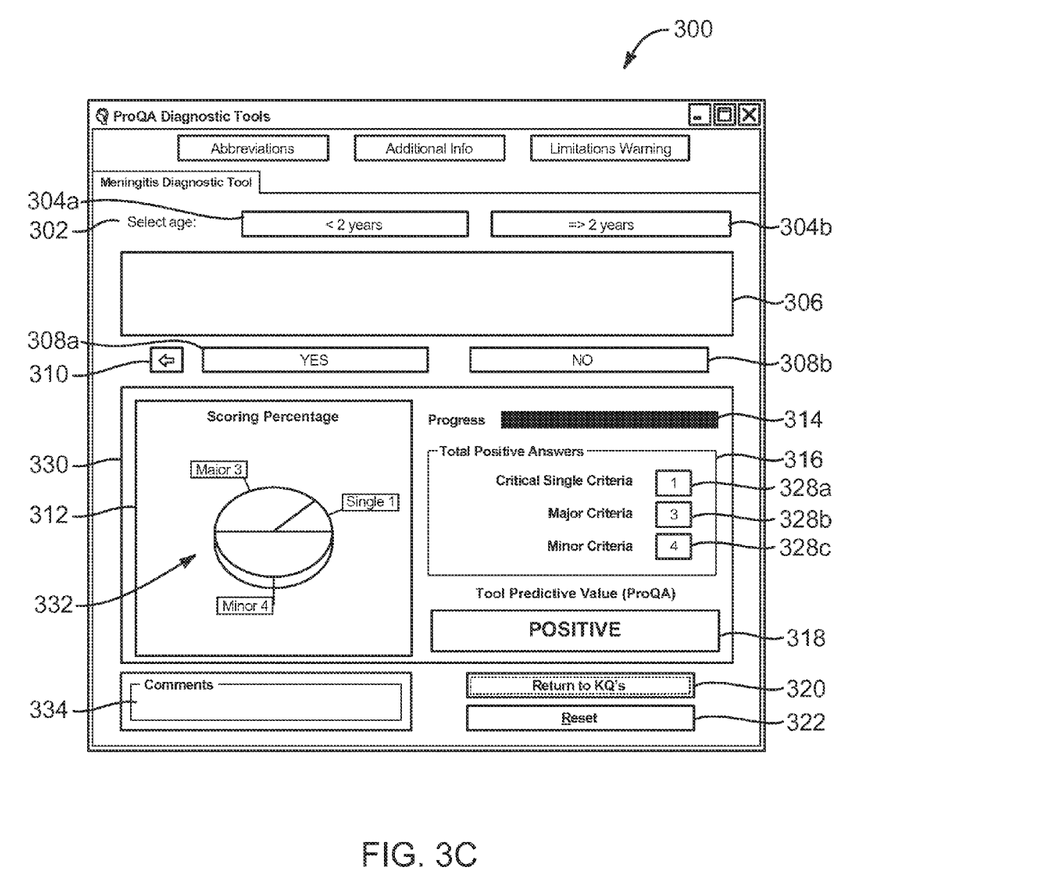

FIGS. 3A-3C illustrate an embodiment of a user interface 300 of a meningitis diagnostic tool, according to one embodiment. Referring collectively to FIGS. 3A-3C, the user interface 300 provides one or more instructions 302 to the dispatcher, age classification input components 304a, 304b, a questions pane 306, response input components 308a, 308b, a navigation input component 310, a diagnostic indicators pane 312, a progress indicator 314, a criteria summary pane 316, a recommendation field 318, a return input component 320, and a reset input component 322. The user interface 300 may also present a scoring percentage pane 330 (FIG. 3C) to concisely summarize the severity of the positive factors.

As previously mentioned, the user interface 300 is configured to assist a dispatcher in determining the likelihood that a patient has meningitis. When an emergency caller reports that a patient is suspected to have meningitis, or otherwise reports symptoms that raise concern that the patient may have meningitis, the appropriate level of emergency response may depend largely on the likelihood that the patient has meningitis. A difficulty arises in that often emergency callers are not skilled in identifying symptoms or other indicators that are factors used in determining or assessing the likelihood that the patient has meningitis. Accordingly, a question from the dispatcher, such as "Do you think the patient may have meningitis?," may not successfully elicit the information the dispatcher may need to dispatch an appropriate emergency response. Similarly, the dispatcher may lack skill and experience to properly inquire and guide the caller in identifying (and weighing) symptoms and other indicators that are factors used in determining or assessing the likelihood that the patient has meningitis.

The user interface 300 of a meningitis diagnostic tool, according to one embodiment of the present disclosure may provide a pre-scripted interrogation of questions that help identify indicators that can be used to determine whether the patient may have meningitis. The user interface 300 receives input corresponding to, or otherwise indicative of, the various identified indicators and uses the input to determine a likelihood that the patient has meningitis, or to otherwise make a determination whether the patient has meningitis. The determination can be conveyed to the dispatcher via the user interface and/or conveyed to the emergency dispatch system. The manner by which the meningitis diagnostic tool can aid in determining the likelihood that a patient has meningitis will be made apparent by the following description of the illustrated embodiment of the user interface 300 of a meningitis diagnostic tool, according to one embodiment.

The user interface 300 may present one or more instructions intended to guide the dispatcher in using the tool. In the illustrated embodiment, the user interface 300 provides an instruction 302, such as "Select age," to request that the dispatcher classify the patient into an age grouping. Meningitis may manifest itself differently in children under two years of age than in adults and children over two years of age. Accordingly, the diagnostic tool may function differently based on the age of the patient, and the diagnostic tool may seek information regarding the patient's age grouping to determine how to function. Age information of the patient may be communicated to the diagnostic tool by the emergency dispatch system, if the age information was previously obtained during processing of the call. The user interface 300 also provides one or more age classification input components 304a, 304b to allow the dispatcher to provide the information to the diagnostic tool. As can be appreciated, the dispatcher may need to ask the caller the age of the patient if this information is not known. However, the configuration of the instruction 302 and age classification input components 304a, 304b of the user interface 300 provide intuitive guidance to the dispatcher to gather and/or provide information to the diagnostic tool concerning the patient's age or age grouping.

In the illustrated embodiment, the age classification input components 304a, 304b are buttons that the dispatcher can click to quickly and efficiently designate the age grouping of the patient. FIG. 3A illustrates the user interface 300 prior to the dispatcher providing age classification input to the diagnostic tool. The age classification input components 304a, 304b include a label to clearly indicate to the dispatcher the information that will be entered by operating the button. For example, a first age classification input component 304a includes a label "<2 years" to indicate that clicking on the input component 304a enters information to the diagnostic tool that the patient is less than two years old. A second age classification input component 304b includes a label "=>2 years" to indicate that clicking on the input component 304b enters information to the diagnostic tool that the patient is two years old or older. As can be appreciated, in another embodiment, the age classification input components 304a, 304b are not limited to buttons and may include, for example, familiar user interface components, including but not limited to text fields, text boxes, menus, drop-down menus, drop-down selection boxes, lists, buttons, check boxes, and radio buttons, or any combination thereof.

The questions pane 306 presents one or more questions 324 (FIG. 3B) to the dispatcher. The questions 324 may include caller questions intended to be relayed by the dispatcher to the caller, to aid the dispatcher in guiding the caller to identify indicators that the patient has meningitis. The questions 324 may also include dispatcher (or call taker) questions directed solely to the dispatcher. FIG. 3B illustrates the user interface 300 presenting a question 324 in the questions pane 306. In the illustrated embodiment, the questions are presented serially, with only one question 324 displayed at a time. As can be appreciated, other presentation forms are possible, including but not limited to presenting an entire listing of questions along with an indication of a current question.

The questions 324 generally may relate to identifying indicators that the patient has meningitis. For example, in FIG. 3B the question presented is "Is s/he vomiting?". Other questions 324 that may be presented may include, but are not limited to, the following: "Does s/he have a rash?", "Is it [the rash] splotched (mottled) or looking like a bruise?", "Is s/he crying?", "Does s/he have a shrill or strange cry?", "Does s/he appear sleepy or not alert?", "Is s/he refusing to feed?", "Is s/he distressed by bright lights?", "Are her/his hands or feet cold to the touch?", and "Did s/he ever stop breathing or turn blue?". The particular questions presented, and the order in which they are presented, may depend on previously entered input. For example, the questions 324 that are presented may depend on the age group of the patient. As another example, the questions presented may depend on responses to previously presented questions, such that whether a particular question is presented may depend upon caller responses to earlier presented questions (e.g. whether the question "Is it [the rash] splotched (mottled) or looking like a bruise?" is presented may depend on the answer to the question "Does s/he have a rash?"). The diagnostic tool may traverse a logic tree that defines which questions are presented in which order, as discussed more fully below with reference to FIG. 4. By traversing a logic tree, the meningitis diagnostic tool can provide an orderly and predictable pre-scripted interrogation to gather pertinent information, enabling a more complete and detailed understanding of the patient.

The questions pane 306 may also present one or more dispatcher questions (or call taker questions) directed to the dispatcher or other call taker. These dispatcher questions are intended to not be relayed to the caller. Rather, the dispatcher questions prompt the dispatcher to enter information known by or otherwise readily available to the dispatcher. The user interface 300 may provide an indication of which questions 324 presented in the questions pane 306 are intended for the caller (caller questions) and which questions are intended for the dispatcher (dispatcher questions). For example, dispatcher questions may be presented in a different color than the caller questions. Caller questions may be presented in black text while dispatcher questions may be presented in blue text. Examples of dispatcher questions may include, but are not limited to, "Did the caller report that the glass/blanch test was performed?" and "Did the caller ever say anything like 'S/he [the patient] doesn't look right?'".

The response input components 308a, 308b (collectively 308) provided by the user interface allow the dispatcher to quickly enter the caller's response to the question 324 presented in the questions pane 306. Regardless of whether the questions 324 are caller questions or dispatcher questions, the response input components 308a, 308b enable the dispatcher to enter input associated with a presented question 324.

In the illustrated embodiment, the response input components 308 are buttons that can be clicked to enter an associated input. For example, a first response input component 308a can be clicked to enter a "Yes" response to the question 324 presented in the questions pane 306 and a second input component 308b can be clicked to enter a "No" response to the question 324 presented in the questions pane. As can be appreciated, in another embodiment, the response input components 308 may correspond to input (i.e., responses to the questions) other than "Yes" and "No." For example, the response input components 308 may present a plurality of choices (e.g., "Never," "Occasionally," "Often," "Always"). As can also be appreciated, in another embodiment, the response input components 308a, 308b are not limited to buttons and may include, for example, familiar user interface components, including but not limited to text fields, text boxes, menus, drop-down menus, drop-down selection boxes, lists, buttons, check boxes, and radio buttons, or any combination thereof.

When the last question 324 has been presented and input has been provided by the dispatcher, the diagnostic tool may use the input to make a determination whether the patient has meningitis. The determination may be presented in the recommendation field 318, as will be described below. The user interface 300 can also provide interaction with other functionality of the diagnostic tool.

The navigation input component 310 provided by the user interface 300 enables the dispatcher to go back to a previous question. In the illustrated embodiment, the navigation input component 310 is a button that a dispatcher can click on to change the question presented back to the previous question that was presented. As can be appreciated, in another embodiment, a plurality of navigation input components 310 may be provided, including a back navigation input component and a forward navigation input component.

The diagnostic indicators pane 312 displays the diagnostic indicators 326 (FIG. 3B) (e.g., signs, symptoms, conditions, circumstances, or other criteria) of meningitis that are gathered through the dispatcher-entered input. The diagnostic indicators pane 312 enumerates the indicators gathered via dispatcher-entered input that suggest the patient may have meningitis. Because the dispatcher-entered input corresponds to caller-relayed responses to the questions 324, the diagnostic indicators pane 312 may also provide a concise summary of the caller's responses to the questions 324.

In the illustrated embodiment shown in FIG. 3B, the diagnostic indicators pane 312 provides the indicators 326 "Rash," "Splotched," "Glass/blanch test performed," and "Refusing to feed." As can be appreciated, other indicators are possible, including but not limited to, "Crying," Shrill/strange cry," "Sleepy/not alert," "Vomiting," "Distressed by bright lights," "Hands or feet cold to the touch," "Stopped breathing/turned blue," and "Doesn't look right." In the illustrated embodiment, the diagnostic indicators pane 312 displays only the positive indicators, and omits mention of any indicator that is not present. In another embodiment, all relevant indicators 326 may be presented in the diagnostic indicators pane 312, and the positive indicators may be distinguished from the negative indicators.

The progress indicator 314 provides a dispatcher with an easy and intuitive display of the progress of collecting information (including indicators) helpful to assessing whether the patient has meningitis. In FIG. 3A, the progress indicator 314 is empty, indicating that prior to receiving input categorizing the age of the patient, no progress has been made. In FIG. 3B, the progress indicator 314 is partially filled, indicating that progress has been made in collecting information (including indicators) helpful to assessing whether the patient has meningitis. In FIG. 3C, the progress indicator 314 is completely filled, indicating the entire progression of the diagnostic tool is complete. Stated differently, the progress indicator 314 can indicate progression of the diagnostic tool along a logic tree. When the progress indicator 314 indicates progress is complete, progression of the logic tree may be complete.

Referring again collectively to FIGS. 3A-3C, and specifically to FIG. 3C, the criteria summary pane 316 presents a concise tally of the type of positive indicators received that indicate the patient may have meningitis. The criteria summary pane 316 provides one or more tally fields 328a, 328b, 328c (collectively 328) that display a tally of one or more types of indicators. The tally displayed in a tally field 328a, 328b, 328c concisely communicates, for example to a dispatcher, a basis for a likelihood that a patient has meningitis. A tally can be an objective value that quantifies the factors in favor of a determination or diagnosis that the patient has meningitis.

In the illustrated embodiment, a plurality of tally fields 328 are presented to provide tallies of indicators in a plurality of ranges of severity. Some of the indicators of meningitis may be more determinative, or more strongly suggest a likelihood that the patient has meningitis, than other indicators. For example, some indicators alone may be critical indicators because they may be substantially determinative that the patient has meningitis. A tally labeled "Critical Single Criteria" may be helpful to indicate, for example to the dispatcher, the number of these critical indicators that are present with the patient. A first tally field 328a may present the tally of critical indicators. Other indicators may be strong indicators, but not solely determinative. A tally "Major Criteria" may be helpful to indicate the number of strong indicators. A second tally field 328b may present the tally of strong indicators. Finally, a number of minor indicators, cumulatively, may strongly suggest that the patient has meningitis. A tally "Minor Criteria" may be helpful to indicate the number of minor indicators. A third tally field 328c may present the tally of minor indicators. The plurality of tally fields 328 can provide insight to the dispatcher as to how and why the diagnostic tool reaches a particular result (or diagnosis). The plurality of tally fields 328 can provide a summary explanation of why a patient may have meningitis.

As an example, the critical indicators that may be substantially determinative and counted in the tally "Critical Single Criteria" may include: a positive glass test, stopped breathing, turned blue, and "doesn't look right" and the patient is under 2 years of age.

As another example, the strong indicators that may be counted in the tally "Major Criteria" for a patient under 2 years of age may include: a rash with a positive glass test, the patient is limp or like a rag doll, the patient "doesn't look right", stopped breathing, turned blue, the patient is sleepy or not alert, a splotched or bruised rash and no glass test performed.

As another example, the strong indicators that may be counted in the tally "Major Criteria" for a patient 2 years of age or older may include: a rash with a positive glass test, a stiff neck, the patient is limp or like a rag doll, the patient is confused or not alert, "doesn't look right", a splotched or bruised rash and no glass test performed.

As another example, the minor indicators that cumulatively may strongly suggest meningitis and may be counted in the tally "Minor Criteria" for a patient under 2 years of age may include: a rash with no glass test performed, a shrill or strange cry, refuses to feed, vomiting, distressed by bright lights, and hands or feet are cold to the touch.

As another example, the minor indicators that cumulatively may strongly suggest meningitis and may be counted in the tally "Minor Criteria" for a patient 2 years of age or older, may include: a rash with no glass test performed, avoids bright lights, severe headache, nausea or vomiting, and hands or feet are cold to the touch.

In the illustrated embodiment, the tally fields 328 provide a final tally, after progression of the diagnostic tool is complete. Accordingly, the tally fields 328 in FIG. 3B display a tally of "0" for each of the types of indicators, despite a number of positive indicators being recorded in the diagnostic indicators pane 312. Displaying only a final tally can provide clarity that a tally is not complete. However, as can be appreciated, in other embodiments, the tally fields 328 may provide a running tally of positive indicators that have been received. A running tally may allow a dispatcher to anticipate a diagnosis or result of the diagnostic tool, enabling the dispatcher to prepare for the next steps in processing the emergency call.

The user interface 300 may also present a scoring percentage pane 330 to concisely summarize the severity of the positive factors, as shown in FIG. 3C. In the illustrated embodiment, the scoring percentage pane 330 is presented in place of the diagnostic indicators pane 312, after dispatcher-entered input is provided for the last question. The scoring percentage pane 330 may provide a pie-chart 332 or other relative depiction to indicate what scoring percentage contributed to the determination by the diagnostic tool that the patient does or does not have meningitis. The pie-chart 332 may provide a more graphically visual way of showing the indicators listed in the criteria summary pane 316.

The recommendation field 318 provides an indication to the dispatcher of a recommendation and/or a determination made by the diagnostic tool as to whether the patient has meningitis. In FIG. 3C, the recommendation field 318 presents a recommendation or indication "SIGNIFICANT Evidence" to indicate that the diagnostic tool has determined that there is significant evidence, and/or a high likelihood, that the patient has meningitis. The recommendation field 318 may also present a recommendation or indication "PARTIAL Evidence" to indicate that the diagnostic tool has determined that there is some evidence that the patient has meningitis. The recommendation field may also present a recommendation or indication "NO TEST Evidence" to indicate that there is not sufficient evidence, or no determined or discovered evidence, to determine that the patient has meningitis. As can be appreciated, other recommendations are possible, including but not limited to "NEGATIVE" to indicate that the patient likely does not have meningitis.

A scoring formula may be included to score the criteria and make a determination of the recommendation to present. As an example, the following scoring formula (s) may be used by the tool to determine a recommendation to present in the recommendation field 318:

SIGNIFICANT Evidence if:
Any Single Critical indicators are present, OR
Two Major indicators are present, OR
One Major indicator and two or more Minor indicators are present.
PARTIAL Evidence if:
One Major indicator and one Minor indicator are present, OR
Three or more Minor indicators are present.
NO TEST Evidence if:
No Major or Minor indicators are present, OR
Two or fewer Minor indicators are present.

Other scoring formula (s) may be used. The scoring formula (s) may also evolve, changing over time as accuracy of the prediction of outcomes is assessed and improvements are made in diagnosing meningitis.

A return input component 320 is also presented to the dispatcher by the user interface 300 to close the diagnostic tool and/or diagnostic tool user interface 300, and return processing and/or control to the medical dispatch protocol. In the depicted embodiment, the return input component 320 is provided as a button that the user can click on and that is labeled "Return to KQs." The dispatcher clicks the return input component 320 button to close the meningitis diagnostic tool. In another embodiment, the return input component 320 may also signal to the diagnostic tool to transfer the recommendation and/or the information provided concerning the patient's diagnostic instruction responses to the emergency medical dispatch protocol and/or determinant value calculator, prior to the diagnostic tool closing.

In another embodiment, a close input component may be presented to the dispatcher by the user interface 300 to close the diagnostic tool and/or diagnostic tool user interface 300. The close input component may be provided as a button that the user can click on to close the meningitis diagnostic tool. The close input component may also signal to the diagnostic tool to transfer the recommendation and/or the information provided concerning the caller's responses and/or the patient responses to the emergency medical dispatch protocol and/or determinant value calculator, prior to the diagnostic tool closing.

A reset input component 322 is also provided by the user interface 300 of FIGS. 3A-3C to allow a dispatcher to reset the user interface 300. The reset input component 322 may clear all dispatcher-entered input from the user interface 300 and/or the diagnostic tool. The reset input component 322 also moves progression along the logic tree back to the beginning, essentially starting the diagnostic tool over.

A comments field 334 may be provided to display additional information and/or comments regarding a particular indicator, or alternatively a plurality of indicators. As can be appreciated, additional user interface components and functionality can be provided.

Figure 4:
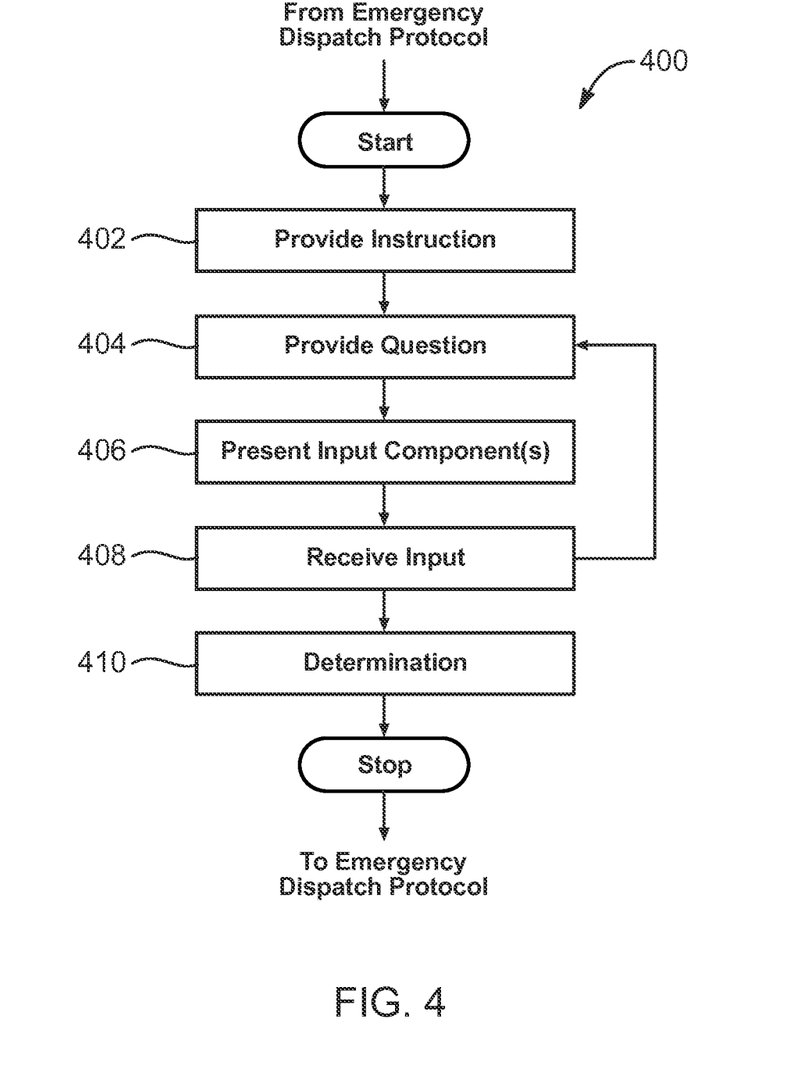
FIG. 4 is a high-level flow diagram of a protocol 400 of a meningitis diagnostic tool, according to one embodiment.

FIG. 4 is a high-level flow diagram of a protocol 400 of a meningitis diagnostic tool, according to one embodiment. The meningitis diagnostic may be initiated (e.g., launched) from within the emergency dispatch protocol. The emergency dispatch protocol may automatically launch the tool based on input received by the emergency dispatch protocol indicating that the patient may have meningitis. The meningitis diagnostic tool may also be launched manually, as desired, by the dispatcher. Upon launching, the meningitis diagnostic tool may present a user interface.

The protocol 400 may provide 402 an instruction to the dispatcher, such as an instruction to select the age, or an age category, of the patient. The protocol 400 may also provide 404 a question for the dispatcher to direct to the caller to gather information concerning the indicators whether the patient may have meningitis. The protocol 400 also presents 406 one or more input component(s) to enable the dispatcher to provide the protocol with input corresponding to a caller response to the question and the protocol receives 408 the dispatcher-entered input. The protocol 400 may provide 404 additional questions, present 406 one or more input component(s) for entering input corresponding to responses to those additional questions, and receive 408 the dispatcher-entered input. The protocol 400 may make a determination 410 as to whether the patient likely has meningitis based on the input received 408. After the determination 410 is made, the logic flow of the protocol 400 ends and control is transferred back to the emergency dispatch protocol.

Figure 5:
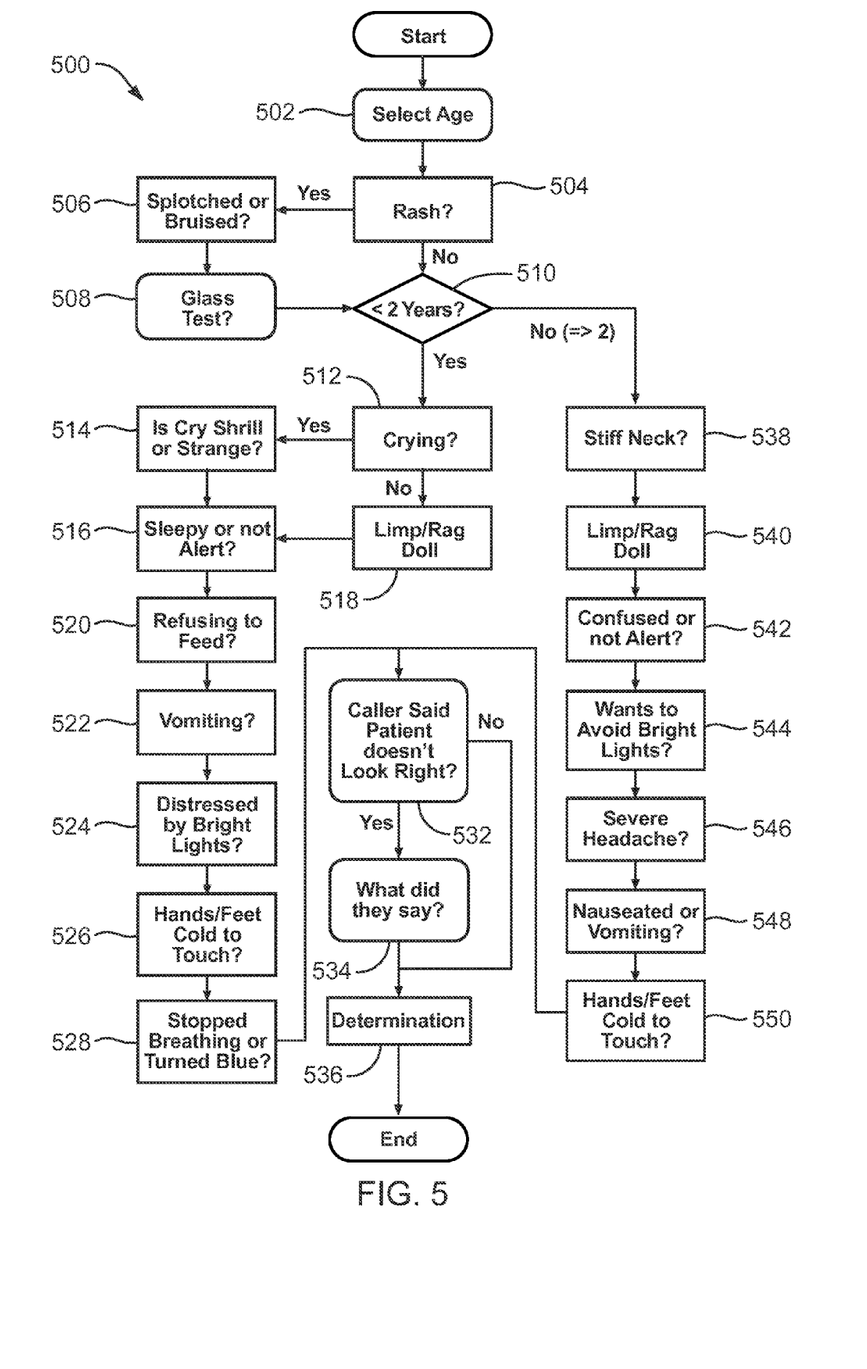
FIG. 5 is a flow diagram of a protocol of a meningitis diagnostic tool, according to one embodiment.

FIG. 5 is a flow diagram of one embodiment of a protocol 500 of a meningitis diagnostic tool. An instruction may be provided to the dispatcher to select 502 the age of the patient. As described above, age classification input components 304a, 304b (see FIG. 3A) may be provided for the dispatcher to select 502 the age of the patient. As can be appreciated, the meningitis diagnostic tool receives input from the dispatcher corresponding to instructions and questions, as was explained above with reference to FIGS. 3A-3C and FIG. 4. The input may be received substantially in real-time, as the dispatcher provides the input. Alternatively, or in addition, the input may be received from the emergency medical dispatch system because information sought by the protocol may have previously been obtained from the dispatcher via the emergency dispatch protocol. Alternatively, or in addition, the input may be received from a different diagnostic tool. While explicit steps of receiving information are not depicted in FIG. 5, an ordinarily skilled artisan will recognize that input may be received at various points in the protocol 500 of the meningitis diagnostic tool.

The protocol 500 may question 504 the caller (e.g., present a question to the dispatcher for relay to the caller), "Does the patient have a rash?" If the patient has a rash, the protocol may question 506, "Is the rash splotched (mottled) or looking like a bruise?". The dispatcher may then be questioned 508, "Did the caller report that the glass/blanch test was performed." Questioning 508 the dispatcher, rather than the caller, regarding the glass/blanch test may allow gathering information about this useful test for diagnosing meningitis from a caller already familiar with the test and its significance, yet avoid a tedious explanation to a caller who is not familiar with the test or is otherwise untrained in the medical field. Questions directed to the dispatcher may be indicated, or otherwise differentiated from questions directed to the caller, so as to clearly convey to the dispatcher which questions are to be conveyed to the caller. For example, questions to the dispatcher may be presented in a different color, such as blue, than the color in which caller questions are presented, such as black.

After questioning 508 the dispatcher regarding the glass/blanch test, or if the patient does not have a rash, the protocol 500 may determine 510 the patient's age category, such as whether the patient is under two years of age, or two years of age or older, based on input received in response to the dispatcher selecting 502 the age category of the patient. Alternatively, the protocol 500 may also determine 510 the patient's age category based on information received from an emergency dispatch system and relayed to the meningitis diagnostic tool.

If the patient is less than two years of age, the protocol 500 may proceed with a branch of questions different than if the patient is two years of age or older. In the illustrated embodiment, if the patient is less than two years of age, the protocol 500 may question 512 the caller, "Is the patient crying?" If the patient is not crying, the caller may be questioned 518, "Is the patient limp or like a rag doll?" If the patient is crying, the caller may be questioned 514, "Is the cry shrill or strange?"

After questioning 518 if the patient is limp or like a rag doll or questioning 514 if the cry of the patient is shrill or strange, the protocol 500 may question 516, "Is the patient sleepy or not alert?" The protocol may provide other questioning, such as a question 520, "Is the patient refusing to feed?," a question 522, "Is the patient vomiting?", a question 524, "Is the patient distressed by bright lights?," a question 526, "Are the patient's hands or feet cold to the touch?," and a question 528, "Has the patient stopped breathing or turned blue?".

The protocol 500 may further question 532 the dispatcher, "Did the caller ever say anything like 'S/he doesn't look right'?". If the dispatcher enters input that the caller did say something similar, the protocol may further question 534 the dispatcher, "What did s/he say?," and present an input field in which the dispatcher can enter what the caller said. If the dispatcher enters input that the caller did not say anything similar, or after the protocol 500 receives what the caller said, the protocol 500 may make a determination 536 of the likelihood that the patient has meningitis. As described above, the determination 536 whether the patient has meningitis may be based on one or more tallies of indicators in one or more categories or ranges of severity. The determination may be displayed to the dispatcher and/or communicated to the emergency dispatch protocol and/or emergency responders.

If the patient is two years of age or older, the protocol 500 may proceed with a branch of questions different than if the patient is less than two years of age. In the illustrated embodiment, if the patient is two years of age or older, the protocol 500 may provide questioning such as a question 538, "Does the patient have a stiff neck?", a question 540, "Is the patient limp or like a rag doll?", a question 542, "Is the patient confused or not alert?", a question 544, "Does the patient want to avoid bright lights?", a question 546, "Does the patient have a severe headache?", a question 548, "Is the patient nauseated or vomiting?", and a question 550, "Are the patient's hands or feet cold to the touch?".

As before, the protocol 500 may further question 532 the dispatcher, "Did the caller ever say anything like 'S/he doesn't look right'?". If the dispatcher enters input that the caller did say something similar, the protocol may further question 534 the dispatcher, "What did s/he say?," and present an input field in which the dispatcher can enter what the caller said. If the dispatcher enters input that the caller did not say anything similar, or after the protocol 500 receives what the caller said, the protocol 500 may make a determination 536 of the likelihood that the patient has meningitis. As described above, the determination 536 whether the patient has meningitis may be based on one or more tallies of indicators in one or more categories or ranges of severity. The determination may be displayed to the dispatcher and/or communicated to the emergency dispatch protocol and/or emergency responders.

The embodiments described above, as previously mentioned, may transfer or otherwise communicate a result of the determination whether the patient has meningitis to the emergency medical dispatch protocol and/or the determinant value calculator to aid in determining the priority of the dispatch response. The result of the determination whether the patient has meningitis may be incorporated into the traversal of the logic tree of the emergency dispatch protocol. For example, subsequent decisions as to how the emergency dispatch protocol proceeds along the logic tree may be based, at least in part, upon the determination whether the patient has meningitis of the meningitis diagnostic tool. In another embodiment, the result of the determination whether the patient has meningitis and/or input to the meningitis diagnostic tool may be communicated to other components of the emergency medical dispatch system 100 as well. Moreover, other information may be communicated as well. All information gathered by the diagnostic tools 120 may be stored by the emergency medical dispatch system 100 and conveyed to the determinant value calculator 110, the reporting module 114, the CAD system 112, and/or to trained emergency responders. This information may be used to assist emergency responders prior to arrival. The diagnostic tools 120, including the meningitis diagnostic tool 122, greatly improve information collection and intervention for emergency medical response situations and aid in saving lives.

While specific embodiments and applications of the disclosure have been illustrated and described, it is to be understood that the disclosure is not limited to the precise configuration and components disclosed herein. Various modifications, changes, and variations apparent to those of skill in the art may be made in the arrangement, operation, and details of the methods and systems of the disclosure without departing from the spirit and scope of the disclosure.

What is claimed is:

1. A computer-implemented method performed on a dispatch center computer to assist a dispatcher when communicating with a caller via telephone regarding a medical emergency of a patient, comprising:
    providing on the dispatch center computer system an emergency dispatch protocol to assist the dispatcher, the protocol presenting a plurality of pre-scripted interrogatories for the dispatcher to ask the caller to gather information regarding the emergency and generate an emergency dispatch response by emergency responders;
    initiating a diagnostic tool on the dispatch center computer, the diagnostic tool configured to assist the dispatcher in guiding the caller to obtain information that can be used by the diagnostic tool to diagnose whether the patient has meningitis;
    the diagnostic tool presenting to the dispatcher a user interface comprising a diagnostic indicators pane and a criteria summary pane;
    the diagnostic tool providing one or more questions via the user interface, the questions being intended for the dispatcher to vocally relay to the caller over the telephone to guide the caller in identifying signs and symptoms that the patient has meningitis;
    the diagnostic tool receiving dispatcher-entered input indicative of caller-relayed information concerning the caller's observations of the patient, including signs and symptoms that indicate whether the patient has meningitis, wherein the caller's observations are vocally relayed over the telephone to the dispatcher;
    presenting, on the diagnostic indicators pane of the user interface of the diagnostic tool, a listing of one or more signs and symptoms that indicate whether the patient has meningitis that are received through the dispatcher-entered input;
    presenting, on the criteria summary pane of the user interface of the diagnostic tool, a plurality of tally fields to convey a basis for a likelihood that the patient meningitis, each tally field of the plurality of tally fields displaying a tally of signs and symptoms of a level of severity that is different from a level of severity corresponding to other of the plurality of tally fields; and
    the diagnostic tool determining a likelihood that the patient has meningitis based on the dispatcher-entered input indicative of the caller-relayed information and the tallies of signs and symptoms displayed by the plurality of tally fields.

2. The computer-implemented method of claim 1, further comprising the diagnostic tool indicating to the dispatcher, via the user interface, a result of the determination whether the patient has meningitis.

3. The computer-implemented method of claim 1, further comprising:
    the diagnostic tool generating a recommendation that can be relayed to the emergency responders based on a result of the determination whether the patient has meningitis; and
    displaying on the user interface of the diagnostic tool the recommendation.

4. The computer-implemented method of claim 1, wherein the dispatch center computer system initiates the diagnostic tool based on dispatcher-entered input indicative of one or more responses of the caller to the interrogatories presented to the dispatcher by the emergency dispatch protocol.

5. The computer-implemented method of claim 1, further comprising the diagnostic tool communicating to the emergency dispatch protocol a result of determining a likelihood that the patient has meningitis.

6. The computer-implemented method of claim 5, further comprising the dispatch center computer system determining a priority for the emergency dispatch response based on a result of the diagnostic tool determining a likelihood that the patient has meningitis.

7. The computer-implemented method of claim 6, wherein the dispatch center computer system determining the priority further comprises determining a determinant value.

8. The computer-implemented method of claim 1, further comprising the dispatch center computer system presenting to the dispatcher an emergency dispatch protocol user interface having a diagnostic tool launch input to initiate the diagnostic tool, wherein the dispatch center computer system initiates the diagnostic tool in response to actuation of the diagnostic tool launch input.

9. The computer-implemented method of claim 1, wherein the one or more questions provided by the user interface for the dispatcher to vocally relay to the caller comprise a question asking if the patient has a rash.

10. The computer-implemented method of claim 1, wherein the one or more questions provided by the user interface for the dispatcher to vocally relay to the caller comprise a question asking if the patient has a stiff neck.

11. The computer-implemented method of claim 1, wherein the one or more questions provided by the user interface for the dispatcher to vocally relay to the caller comprise a question asking if the patient is limp or acting like a rag doll.

12. The computer-implemented method of claim 1, wherein the one or more questions provided by the user interface for the dispatcher to vocally relay to the caller comprise a question asking if the patient appears confused or not alert.

13. The computer-implemented method of claim 1, wherein the one or more questions provided by the user interface for the dispatcher to vocally relay to the caller comprise a question asking if the patient wants to avoid bright lights.

14. The computer-implemented method of claim 1, wherein the one or more questions provided by the user interface for the dispatcher to vocally relay to the caller comprise a question asking if the patient has a severe headache.

15. The computer-implemented method of claim 1, wherein the one or more questions provided by the user interface for the dispatcher to vocally relay to the caller comprise a question asking if the patient is nauseated or vomiting.

16. The computer-implemented method of claim 1, wherein the one or more questions provided by the user interface for the dispatcher to vocally relay to the caller comprise a question asking if the patient's hands or feet are cold to the touch.

17. The computer-implemented method of claim 1, further comprising:
the diagnostic tool providing via the user interface a question directed to the dispatcher; and
the diagnostic tool receiving dispatcher-entered input indicative of a response of the dispatcher to a question directed to the dispatcher.

18. The computer-implemented method of claim 17, wherein the question directed to the dispatcher comprises a question asking if the caller reported that the glass/blanch test was performed.

19. The computer-implemented method of claim 17, wherein the question directed to the dispatcher comprises a question asking if the caller ever said that the patient does not look right.

20. The computer-implemented method of claim 1, the diagnostic tool providing one or more input components via the user interface to receive dispatcher entered-input indicative of an age grouping of the patient, wherein the one or more questions provided by the diagnostic tool via the user interface are dependent on the indicated age grouping of the patient.

21. A computer system to assist a dispatcher when communicating with a caller via telephone regarding a medical emergency of a patient, the computer system comprising:
a processor;
an input device in electrical communication with the processor;
an output device in electrical communication with the processor; and
a memory in electrical communication with the processor, and having stored thereon:
an emergency dispatch protocol including a plurality of pre-scripted interrogatories for the dispatcher to ask the caller to generate an emergency dispatch response; and
a diagnostic tool to assist the dispatcher in guiding the caller to obtain information that can be used by the diagnostic tool to determine a likelihood that the patient has meningitis, wherein the diagnostic tool is configured to present to the dispatcher a user interface comprising:
one or more questions for the dispatcher to vocally relay to the caller over the telephone to guide the caller in identifying signs and symptoms that the patient has meningitis,
one or more input components associated with the one or more questions, the input components to receive dispatcher-entered input indicative of caller-relayed information concerning the caller's observations of the patient, including signs and symptoms that indicate whether the patient has meningitis,
a diagnostic indicators pane to present a listing of one or more signs and symptoms that indicate whether the patient has meningitis that are received through the dispatcher-entered input, and
a criteria summary pane to present a plurality of tally fields to convey a basis for a likelihood that the patient meningitis, each tally field of the plurality of tally fields displaying a tally of signs and symptoms of a level of severity that is different from a level of severity corresponding to other of the plurality of tally fields,
wherein the caller-relayed information is vocally relayed over the telephone to the dispatcher, and
wherein the diagnostic tool determines the likelihood that the patient has meningitis based on tallies of signs and symptoms displayed by the plurality of tally fields on the criteria summary pane.

22. The computer system of claim 21, wherein the diagnostic tool is further configured to provide to the emergency dispatch protocol an indication of a likelihood that the patient has meningitis.

23. The computer system of claim 21, further comprising a determinant value calculator stored on the memory to calculate a determinant value to prioritize an emergency response, wherein the diagnostic tool is configured to provide to the determinant value calculator a likelihood that the patient has meningitis.

24. The computer system of claim 21, further comprising a reporting module stored on the memory to measure how well a dispatcher performs, wherein the diagnostic tool is configured to provide to the reporting module a likelihood that the patient has meningitis.

25. A non-transitory computer-readable storage medium including computer-readable instructions that, when executed by a computing device, cause the computing device to perform operations to assist a dispatcher when communicating with a caller via telephone regarding a medical emergency of a patient, the operations comprising:
providing on the computing device an emergency dispatch protocol to assist the dispatcher, the protocol presenting a plurality of pre-scripted interrogatories for the dispatcher to ask the caller to gather information regarding the emergency and generate an emergency dispatch response by emergency responders;

initiating a diagnostic tool on the computing device, the diagnostic tool configured to assist the dispatcher in guiding the caller to obtain information that can be used by the diagnostic tool to diagnose whether the patient has meningitis; and the diagnostic tool presenting to the dispatcher a user interface comprising one or more questions for the dispatcher to vocally relay to the caller over the telephone to guide the caller in identifying signs and symptoms that the patient has meningitis, comprising one or more input components associated with the one or more questions, and comprising a diagnostic indicators pane and a criteria summary pane;

the diagnostic tool receiving dispatcher-entered input via the input fields of the user interface, the dispatcher-entered input indicative of caller-relayed information concerning the caller's observations of the patient, including signs and symptoms that indicate whether the patient has meningitis, wherein the caller's observations are vocally relayed over the telephone to the dispatcher;

presenting, on the diagnostic indicators pane of the user interface of the diagnostic tool, a listing of one or more signs and symptoms that indicate whether the patient has meningitis that are received through the dispatcher-entered input;

presenting, on the criteria summary pane of the user interface of the diagnostic tool, a plurality of tally fields to convey a basis for a likelihood that the patient meningitis, each tally field of the plurality of tally fields displaying a tally of signs and symptoms of a level of severity that is different from a level of severity corresponding to other of the plurality of tally fields; and the diagnostic tool determining the likelihood that the patient has meningitis based on the dispatcher-entered input indicative of the caller-relayed information and the tallies of signs and symptoms displayed by the plurality of tally fields.

* * * * *